United States Patent [19]

Miyamae et al.

[11] Patent Number: 4,510,942

[45] Date of Patent: Apr. 16, 1985

[54] ELECTRONIC SPHYGMOMANOMETER

[75] Inventors: Ryuichi Miyamae, Osaka; Haruo Yasuda, Yamatokoriyama, both of Japan

[73] Assignee: Sharp Kabushiki Kaisha, Osaka, Japan

[21] Appl. No.: 466,136

[22] Filed: Feb. 14, 1983

[30] Foreign Application Priority Data

| Feb. 15, 1982 | [JP] | Japan | 57-20297[U] |
| Feb. 16, 1982 | [JP] | Japan | 57-20861[U] |
| Feb. 17, 1982 | [JP] | Japan | 57-21913[U] |

[51] Int. Cl.³ .............................................. A61B 5/02
[52] U.S. Cl. .................................... 128/680; 128/683
[58] Field of Search ........................ 128/677, 680–683, 128/687, 689, 696, 701, 710; 381/51, 53

[56] References Cited

U.S. PATENT DOCUMENTS

| 3,565,058 | 2/1971 | Mansfield | 128/701 |
| 3,732,868 | 5/1973 | Willems et al. | 381/51 X |
| 3,760,100 | 9/1973 | Ragsdale et al. | 128/701 X |
| 3,779,235 | 12/1973 | Murphy, Jr. et al. | 128/682 |
| 4,326,536 | 4/1982 | Kitagawa et al. | 128/682 |
| 4,338,490 | 7/1982 | Masuzawa et al. | 381/51 |

Primary Examiner—Lee S. Cohen
Assistant Examiner—Angela D. Sykes
Attorney, Agent, or Firm—Birch, Stewart, Kolasch & Birch

[57] ABSTRACT

A sphygmomanometer is characterized in that, upon completing the blood pressure measuring operation, it automatically informs the operator of the measured values including the systolic and diastolic pressure values stored in a memory circuit by means of synthesized speech. A repeat instruction device prompts repetition of the measured values by synthesized speech, and, when the blood pressure measuring operation is begun, it inhibits the input of the repeat signal so that repeating of verbal information of the measured value is inhibited during a period from the start of pressurizing of the measuring cuff at least until the blood pressure measuring operation is completed.

4 Claims, 7 Drawing Figures

ELECTRONIC SPHYGMOMANOMETER

BACKGROUND OF THE INVENTION

The present invention relates to an improved sphygmomanometer, and more particularly to such a sphygmomanometer that can repeatedly inform an operator of a variety of the measured values such as the systolic and diastolic pressure values and the pulse frequency by means of speech, while after completing these measurements, if necessary, any desired value can be repeated by speech.

Conventionally, when measuring the blood pressure, either a bulb or an automatic air pump is first applied to an arm cuff whereby it is pressurized to suspend the blood circulation, and while the blood pressure measurement is completed, the pneumatic pressure is gradually released from the arm cuff. In such a blood pressure measuring operation, a systolic pressure value is determined at the moment when the first Korotkoff sound is detected, whereas the diastolic pressure value is determined when the last Korotkoff sound is detected.

When using a conventional sphygmomanometer incorporating either a meter or mercury, gage after pressurizing the arm cuff, it is necessary to read from either a meter or mercury gage a systolic pressure value that corresponds to the value when the Korotkoff sound is first detected. It is also necessary to read from either a meter or mercury a diastolic pressure value that corresponds to the value when the Korotkoff sound is lost. In addition, when a blood pressure measuring operation using a conventional sphygmomanometer is completed, the measured values cannot actually be retained, and therefore, the checker must take note of or memorize both the systolic and diastolic pressure values throughout the blood pressure measuring operation.

When a digital sphygmomanometer is used, although it is not necessary to read the measured value to determine either the systolic or diastolic pressure value, the checker still needs to take note of the display value after the measuring operation is completed.

When using a conventional sphygmomanometer, due to any difference that may occur when actually reading the measured value, or due to incorrect reading or careless observation of the display, the checker may incorrectly write such an erroneous data instead of the actual value required.

When a person measures his own blood pressure by operating a sphygmomanometer himself, either reading or writing such a data may adversely affect his own psychology.

A blind man cannot operate such a device by himself to check his own blood pressure, nor gain access to the measured value visually.

OBJECT AND SUMMARY OF THE INVENTION

To effectively solve a variety of problems mentioned above, the present invention provides a sphygmomanometer which is characterized in that; using speech, it informs the checker of the blood pressure value as soon as the blood pressure measuring operation is completed, and if necessary, it repeats speaking of the measured blood pressure values including the systolic and diastolic pressure values and the pulse frequency.

Other objects and further scope of the applicability of the present invention will become apparent from the detailed description given hereinbelow. It should be understood, however, that the detailed description and specific examples, while indicating the preferred embodiments of the present invention, are given by way of illustration only, since a variety of changes and modifications within the scope and spirit of the present invention will become apparent to those skilled in the art from the following detailed description.

To achieve the above object, the present invention embodies a sphygmomanometer comprising; means for detecting the end of the pressure measuring operation, means for repeating speech information so that a plurality of the measured values stored in memory can be audibly repeated in responding to the output from the measuring operation end detect means, means for instructing speech to repeat speaking of a plurality of the measured values, and means activating said speech repeat means in response to an instruction that instructs said speech means to repeat speaking of the measured values, and after completing the blood pressure measuring operation, said means sequentially repeat speaking of the measured values being automatically memorized by memory, and after completing the blood pressure measuring operation, if necessary, any of the measured values can be individually and repeatedly informed by speech.

A still further embodiment of the present invention comprises; means for detecting the end of the blood pressure measuring operation, means for repeating the measured values by speech in responding to the outputs from said detection means, means for reactivating said speech repeat means, means for detecting the start of pressurizing the arm cuff, and means for inhibiting the speech repeat means in responding to the output from the measurement end detect means, enabling the speech repeat inhibit means to inhibit accepting any operation signal output from the repeat instruction means during a period from the start of pressurizing the arm cuff at least until the moment where the blood pressure measuring operation is completed, and then any operation of the repeat instruction means cannot be accepted while the blood pressure measuring operation is still being carried out, whereas the repeat means remains operative when the blood pressure measuring operation is not being performed, and as a result, values obtained from the last measurement can be repeatedly spoken whenever necessary.

BRIEF DESCRIPTION OF THE DRAWING

The present invention will be better understood from the detailed description given hereinbelow and the accompanying drawings which are given by way of illustration only, and thus are not limitative of the present invention and wherein.

DETAILED DESCRIPTION OF THE INVENTION

In reference to the drawings, details of the present invention are described below.

Figure 1:
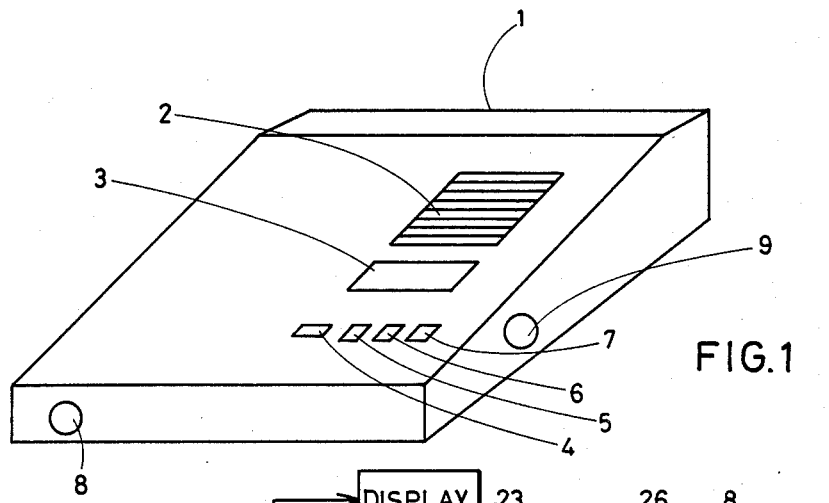
FIG. 1 shows an external perspective view of the sphygmomanometer of a preferred embodiment of the present invention.

FIG. 1 shows an external perspective view of the sphygmomanometer as a preferred embodiment of the present invention.

In reference to FIG. 1, the upper panel of the sphygmomanometer 1 is provided with a speaker 2 that audibly repeats the results of the blood pressure measurement, a display means 3 that displays the results of the measurement as to the systolic and diastolic pressure values and pulse frequencies, a power switch 4, and the repeat instruction keys 5, 6, and 7, each of which activates the repeated speech to inform the operator of any desired value individually as to the results of checking the systolic and diastolic pressure values and/or the pulse frequencies after such measurement results were once spoken upon completing the measuring operation.

The front panel of the sphygmomanometer 1 is provided with a jack 8 for connecting an ear phone. A pressure release speed adjustment knob 9 is provided on the right side panel. Although not illustrated, an air connector is provided on the left side panel and a display switch that turns the display of the display device 3 ON and OFF is provided on the rear panel, which is however not illustrated.

Figure 2:
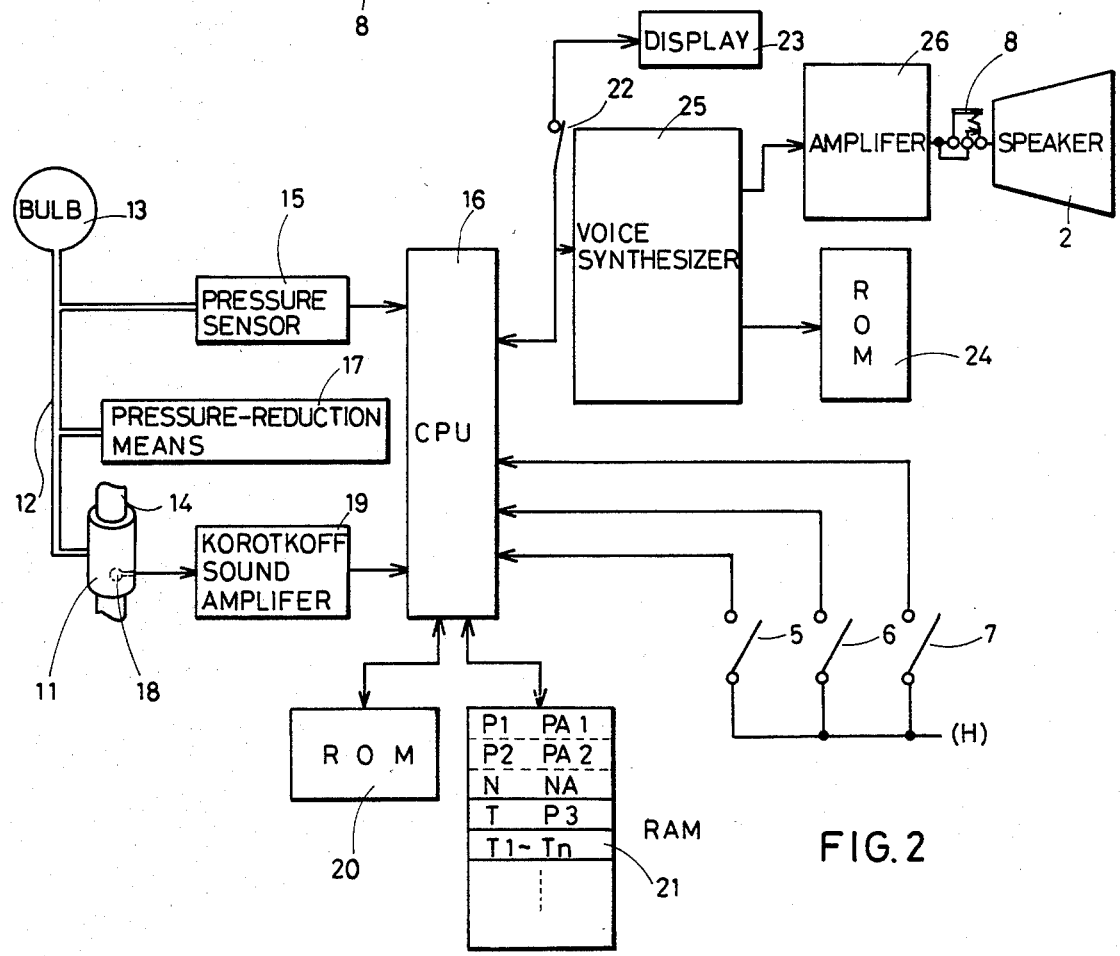
FIG. 2 shows a block diagram representing the construction of the sphygmomanometer of a preferred embodiment of the present invention.

FIG. 2 shows a block diagram representing the construction of a preferred embodiment of the present invention. In reference to FIG. 2, bulb 13 feeds pressurized air into the arm cuff 11 through a pressure hose 12 so that the limb 14 will be pressed tightly. The pressure fed to the arm cuff 11 is then sent to the pressure sensor 15 installed in the sphygmomanometer 1 through an air connector which is also installed in the sphygmomanometer 1. The pressure sensor 15 is composed, for example, of a bellows type sensor, which converts the pressure existing in the arm cuff 11 into an electric signal. The output from this pressure sensor 15 is fed to the microcomputer (CPU) 16, where the input is digitally converted into a pressure value. The pressure reduction means 17 gradually decreases the pressure remaining in the arm cuff 11. The pressure reduction means 17 is composed, for example, of a needle valve, while the speed of decreasing the pressure is adjusted by the pressure release speed adjustment knob 9.

The microphone 18 is, for example, of a ceramic piezoelectric microphone, which detects the Korotkoff sound, and the detected output is then fed to the Korotkoff sound amplifier 19, where even a minimal Korotkoff sound is amplified to a certain amplitude before being fed to the CPU 16.

Figure 3:
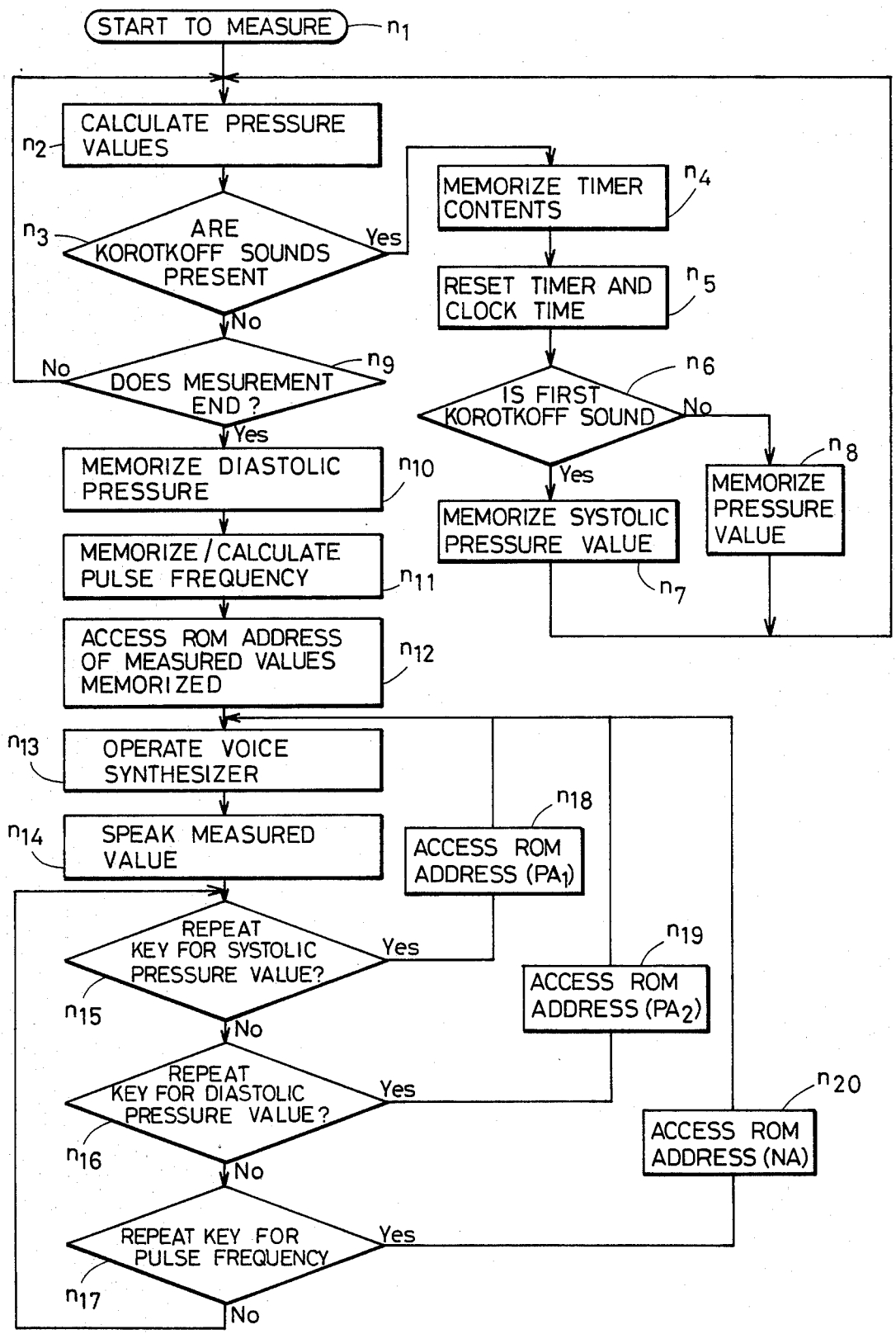
FIG. 3 shows an operational flow chart of the sphygmomanometer according to the present invention.

The CPU calculates the pressure value according to the outputs from the pressure sensor 15 and Korotkoff sound amplifier 19, according to instructions from read-only memory (ROM) 20 that stores the programs of the CPU 16 including the operation steps (operation programs) shown in FIG. 3, while the CPU determines the systolic and diastolic pressure values and the pulse frequency, then the determined values are eventually memorized in areas P1 through P3 and N designated by random access memory (RAM) 21.

The CPU 16 then outputs a plurality of the measured data memorized by RAM 21 to the display 23 through the display switch 22, and then after the CPU 16 identifies that the measurement operation is completed, it converts a plurality of the measured data stored by RAM 21 into the address of the speech data stored in ROM 24, and it eventually outputs said address to the voice synthesizer 25 together with the control signal, and at the same time, the CPU memorizes the converted address of ROM 24 in the areas PA1, PA2, and NA of RAM 21.

Using the control signal and ROM address data fed from the CPU 16, the voice synthesizer 25 reads data from ROM 24, then synthesizes a speech output based on the speech data (speech parameter data) read from ROM 24. Said speech data is then amplified by the amplifier 26 before eventually being output to the speaker 2 through a contact point of the earphone jack 8.

Repeat instruction keys 5, 6, and 7, respectively make it possible to individually select and repeat the systolic or diastolic pressure value or a variety of the values measured against the pulse frequency, while the CPU receives signals that operate these keys.

In reference to the operational flow chart shown in FIG. 3, sequential operation of the sphygmomanometer 1 is described below.

Before starting to measure the pressure values, an air connector on the arm cuff 11 is inserted to the other air connector of the sphygmomanometer 1, and then the arm cuff 11 is wound onto the limb 14. Then, the bulb 13 is repeatedly grasped so that the arm cuff 11 is pneumatically pressurized.

The pressure being applied to the arm cuff 11 is first detected by the pressure sensor 15, then the detected data is converted into an electrical signal, which is then fed to the CPU 16 where the signal is converted into a digital pressure value. ROM 24 outputs both of the address and control signals at specific intervals, which are then fed to the voice synthesizer 25 where they are converted into a voice signal, enabling the speaker 2 to eventually output the pressurized value at such intervals in terms of voice.

While listening to the spoken pressure value, the operator continues the pressurizing operation until the pressure value reaches a certain level, for example, such as being about 30 mmHg higher than the anticipated systolic value. After the operator increases the pressure value to a level about 30 through 40 mmHg higher than the anticipated systolic value of the person being checked while the operator keeps listening to the spoken pressure value, when he stops the pressurizing operation, the pressure reduction means 17 is activated to automatically and gradually decrease the pressure and the CPU 16 detects the state of decreasing the pressure, and as a result, the blood pressure measuring operation will be entered (see FIG. 3 step n-1) and so the sphygmomanometer 1 starts to operate in accordance with the procedures shown in the operational flow chart of FIG. 3.

The pressure value converted into an electrical signal by the pressure sensor 15 during the pressure decreasing period is sequentially fed to the CPU 16, which then calculates the pressure value and converts it into a digital value, as shown in the step n2 of FIG. 3.

As short while after the pressurizing operation is stopped, the microphone 18 detects the Korotkoff sound, which is then amplified by the Korotkoff sound amplifier 19 and then fed to the CPU 16. The CPU 16 checks the Korotkoff sound (step n3) and then determines the Korotkoff sound input so that the counted contents of the timer area of RAM 21 can be memorized by the timer memory areas T1 through TN (step n4), and after the counted contents of the timer area T is reset, the CPU 16 enters the counting operation (step n5). Next, the CPU 15 determines whether the Korotkoff sound, which is input, is the first such sound after the step n6 is entered. If it is the first time, the pressure value calculated during this stage is designated to be the systolic pressure value, this value is then memorized in the systolic pressure value memory area (step n7). If it is not the first Korotkoff sound input, the pressure value during this stage is newly memorized (step n8) by the pressure value memory area P3 of RAM 21, so that the operational mode will return to step n2 in order to repeat the same procedures.

After these operations are repeatedly performed, the counted contents in the timer area T eventually correspond to such values that measured the time intervals of the Korotkoff sound being input, and the contents of which are sequentially memorized in the memory areas T1 through Tn. If the CPU 16 identifies that the Korotkoff sound is not input during the step n3, it then judges during the step n9 whether the blood pressure measuring operation is completed, or not. Specifically, the CPU 16 determines whether the counted contents of the timer T is above a specific value (for example, more than 5 seconds), or not. If the count is below the specific value, the operation sequence again returns to step n2, whereas if the counted contents are above the specific value, the CPU then determines that the blood pressure measuring operation is completed, and then the operation mode proceeds to the step n10. During the step n10, in responding to the Korotkoff sound detected last, the pressure value memorized in the memory area P3 is then memorized in the diastolic pressure memory area P2 as the diastolic pressure value, and then the operation mode proceeds to the step n11, where the pulse frequency is calculated, and the result is memorized in the memory area N of RAM 21.

The pulse frequency is memorized in the memory area T1-TN of RAM21 of the CPU 16, where the pulse frequency is calculated by the time interval data of the Korotkoff sound, for example, the result can be calculated by dividing the numeral "60" by the data (in the second unit) which is the average of a variety of data memorized in the memory areas T1 through TN.

The operation mode then proceeds to the step n12, where the systolic and diastolic pressure values and the pulse frequency memorized in the memory areas P1, P2, and N are then read out by the CPU16, and so the voice data address of ROM 24 corresponding to the measured value read by the CPU16 is calculated, which is then fed to the voice synthesizer 25 together with the control signal, and at the same time, the voice data address is memorized in memory areas PA1, PA2, and NA.

The operation mode then proceeds to the step n13, where the voice synthesizer 25 reads out the memory contents of ROM 24 by means of the control signal and the ROM address data being output from the CPU16, and so the voice signal corresponding to the measured data is synthesized from the voice data (voice parameter data), then the voice signal drives speaker 2, which then sequentially outputs the voice data (step n14, and then the operation mode enters "standby" for the repeat instruction keys 5 through 7.

Thus, if the CPU16 detects that the blood pressure measuring operation is completed during step n9, the operation mode proceeds to the step n10 through n14, and then the systolic and diastolic pressures and the pulse frequency are sequentially and automatically repeated in speech.

For reconfirming the result of the blood pressure measuring operation during a period from the end of the last measuring operation until the next measuring operation starts, a repeat instruction key corresponding to the needed measured value, for example, key 5 that corresponds to the systolic pressure value will be operated. The operative state of key 5 is then detected by CPU16 during step n15, and upon receipt of the operation signal output from said key 5, the CPU 16 then reads (step n18) the voice data address of ROM 24 corresponding to the systolic pressure value memorized in the memory area PA1 of RAM 21, and then the voice data address is fed to the voice synthesizer 25 together with the control signal, and so the operation mode proceeds to step n13.

During step n13, being activated by the control signal output from the CPU 16 and the address data output from ROM 24, the voice synthesizer 25 again reads the memory contents stored in ROM 24 in order to synthesize a voice signal from the voice data (voice parameter data) in responding to the systolic pressure value, and then drives speaker 2 which then repeats (step n14) the systolic pressure value memorized in the memory area P1 in speech.

In such a manner described above, as soon as the CPU 16 detects that the repeat instruction key 5 is pressed during step 15, then the operation mode proceeds to the steps n18, n13, and n14 so that only the systolic pressure value previously spoken is repeated.

After the blood pressure measuring operation is completed and the result of which is spoken, if the repeat instruction key 5 is pressed to repeat speaking of the systolic pressure value if so required until the next blood pressure measuring operation begins, then only the required systolic pressure value will be orally repeated.

If the repeat instruction key 6 is pressed so that the diastolic pressure value is repeated, the operational condition is then detected by the CPU 16 during step n16, and then the operation mode proceeds to the steps n19, n13, and n14, where only the needed diastolic pressure value will be repeated by speech. Likewise, if the repeat instruction key 7 is pressed, the operational condition is then detected by the CPU 16 during step n17, and then the operation mode proceeds to the steps n20, n13, and n14, where only the pulse frequency will be repeated by speech.

The speech contents are fed to the display 23 through the display switch 22 whereby the contents are digitally displayed. When the display switch 22 is turned off, the display 23 (which corresponds to display means 3) turns off the measured value being displayed, and when the earphone is connected to the earphone jack 18, speaker 2 is automatically off.

As a result, the checker can gain access to the measured value being spoken through the earphone without such information being made available to the person being treated.

Figure 4:
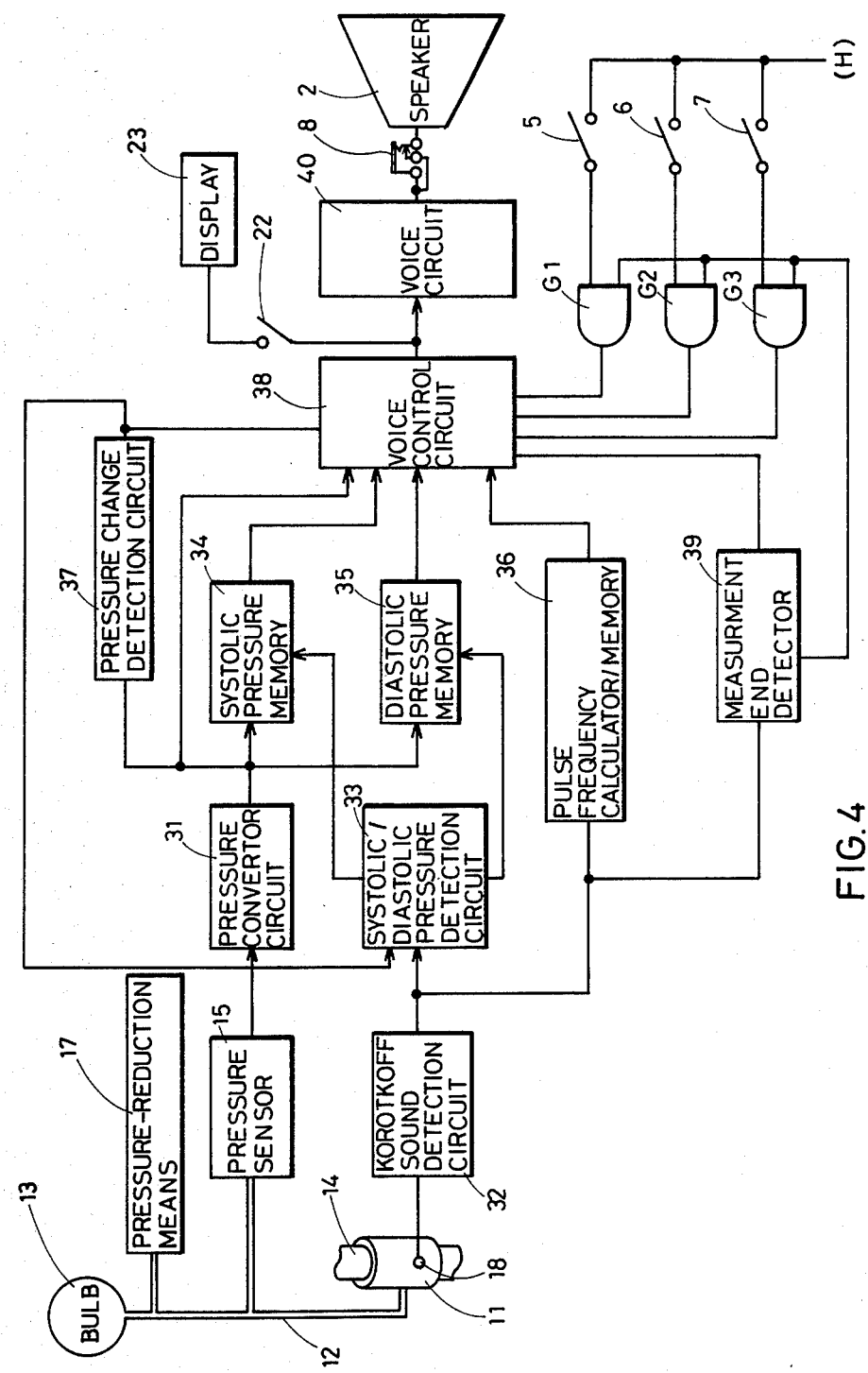
FIG. 4 shows a block diagram of a construction of the sphygmomanometer of another preferred embodiment of the present invention.

FIG. 4 shows a detailed block diagram of another embodiment of the present invention. In FIG. 4, portions identical to FIG. 2 are represented by identical symbols.

The output from the pressure sensor 15 is fed to the pressure conversion circuit 31, where it is converted into a digital pressure value. The output from microphone 18 is fed to the Korotkoff sound detection circuit 32 so that the Korotkoff sound can be detected, and the Korotkoff sound is then fed to the systolic and diastolic pressure detection circuit 33, which then detects the time when the input Korotkoff sound appears (which is the first Korotkoff sound) and also the time when it disappears (which is the last Korotkoff sound), and then designates the pressure values in the pressure conversion circuit 31 as the systolic and diastolic pressure values during the time of detection. Both the systolic and diastolic pressure values are then memorized by the systolic and diastolic pressure memory circuits 34 and 35.

The Korotkoff sound output from the Korotkoff sound detection circuit 32 is fed to the pulse frequency calculation and memory circuit 36, which then calculates and memorizes the pulse frequency according to the intervals of the Korotkoff sound being fed. The pressure change detection circuit 37 detects that the pressure in the arm cuff 11 is either being increased or decreased, and feeds the output that detects the decreasing pressure to the systolic and diastolic pressure detection circuit 33.

Using the Korotkoff sound fed from the Korotkoff sound detection circuit 32, the measurement end detection circuit 39 identifies, for example, a state in which the Korotkoff sound has not been input for more than 5 seconds, and so it detects that the blood pressure measuring operation is terminated. The detected output is then fed to the voice control circuit 38, while the input terminal receives signals that are activated by the repeat keys 5, 6, or 7 which instruct either the systolic and/or diastolic pressure values or the pulse frequency to be repeated, and so the output can be fed to the other input pins of the AND gates G1, G2, and G3 that are connected to the input of the voice control circuit 38.

Said voice control circuit 38 is activated by either the signal indicating that the pressure change detection circuit 37 now provides pressure, or by the measurement end detect signal output from the measurement end detection circuit 39, or in responding to the signal being output from the AND gates G1, G2, and G3. Since the voice control circuit 38 audibly informs of the pressure value converted by the pressure converter circuit 31 or the measured values memorized either the systolic pressure value memory circuit 34, or diastolic pressure value memory circuit 35, or by the pulse frequency calculation and memory circuit 36, the voice control circuit 38 converts data being fed to the ROM address containing the voice data of the voice circuit 40 so that the ROM address corresponding to the input data can be generated by the voice circuit 40, while the voice control circuit 38 also generates a control signal for controlling said voice circuit 40.

The voice circuit 40 is composed of a ROM containing the voice synthesizer and voice data and an amplifier that can be installed if necessary, while said voice circuit 40 reads reads the contents of the ROM by means of a control signal fed from the voice control circuit 38 and the ROM address data so that voice can be synthesized by the voice data (voice parameter data) read therefrom, and the output from the voice circuit 40 then drives speaker 2 which audibly informs of the blood pressure values and the pulse frequency.

When measuring the blood pressure value using a variety of circuits mentioned above, arm cuff 11 is first pressurized by means of a bulb 13. The state of pressurizing the arm cuff 11 is first detected by the pressure change detection circuit 37, then the output from this circuit is fed to the voice control circuit 38, which then converts the pressure value fed from the pressure conversion circuit 31 into the ROM address in the voice circuit 40 corresponding to said pressure value, and as a result, the ROM address signal is fed to the voice circuit 40 together with the control signal at specific intervals, and then said address signal is converted into voice information by means of the voice circuit 40, and so speaker 2 speaks out the blood pressure value at such intervals.

After such a pressurizing operation, for example, if the pressurizing operation is stopped after a pressure is applied to a value which is about 30 mmHg higher than the expected systolic pressure value, then the pressure reduction circuit 17 is activated so that the pressure in the arm cuff 11 is automatically and gradually decreased, and the state of decreasing the pressure is detected by the pressure change detection circuit 37, while the output from this circuit is fed to the systolic and diastolic pressures detection circuit 33, and as a result, a blood pressure measuring operation is performed.

A short while after the pressurizing operation stops, microphone 18 detects the Korotkoff sound, which is then fed to the systolic and diastolic pressures detection circuit 33. This circuit 33 activates the systolic pressure memory circuit 34 to memorize the pressure value which corresponds to the systolic pressure value being output from the pressure converter circuit 31 at the moment when it was determined as the Korotkoff sound detected initially. Pressure is then continuously decreased, enabling the systolic and diastolic pressures detection circuit 22 to determine the time when the Korotkoff sound is lost, and as a result, the pressure value output from the pressure converter circuit 31 when the Korotkoff sound is detected last, is eventually memorized by the diastolic pressure memory circuit 35 as the diastolic pressure value.

The pulse frequency calculation and memory circuit 36 calculates and memorizes the pulse frequency in responding to the incoming Korotkoff sound.

In responding to the signal that indicates the end of the blood measuring operation, being output from the measurement end detection circuit 39, the measured blood pressure value memorized by memory circuits 34, 35, and 36 is then sequentially fed to the voice control circuit 38, and then the voice circuit 40 converts it into the voice data corresponding to the measured blood pressure value so that the systolic and diastolic pressure values and the pulse frequency are informed by speaker 2 by speech.

The output from the measurement end detection circuit 39 opens the AND gates G1 through G3, and during this state, for example, if the repeat key 5 that activates repeated output of the systolic pressure value is pressed, the operation signal is then fed to the voice control circuit 38 via the AND gate G1, which, in responding to this input signal, receives the systolic pressure value memorized in the memory circuit 34, and then outputs a control signal controlling the voice circuit 40 and the ROM address signal. On receipt of this signal, the voice circuit 40 synthesizes the voice signal corresponding to the systolic pressure value, which is then fed to speaker 2 so that only the measured systolic pressure value can be repeated by speech. In the same manner, either the diastolic pressure value or the pulse frequency can be individually repeated by speech by means of the repeat keys 6 and 7.

Figure 5:
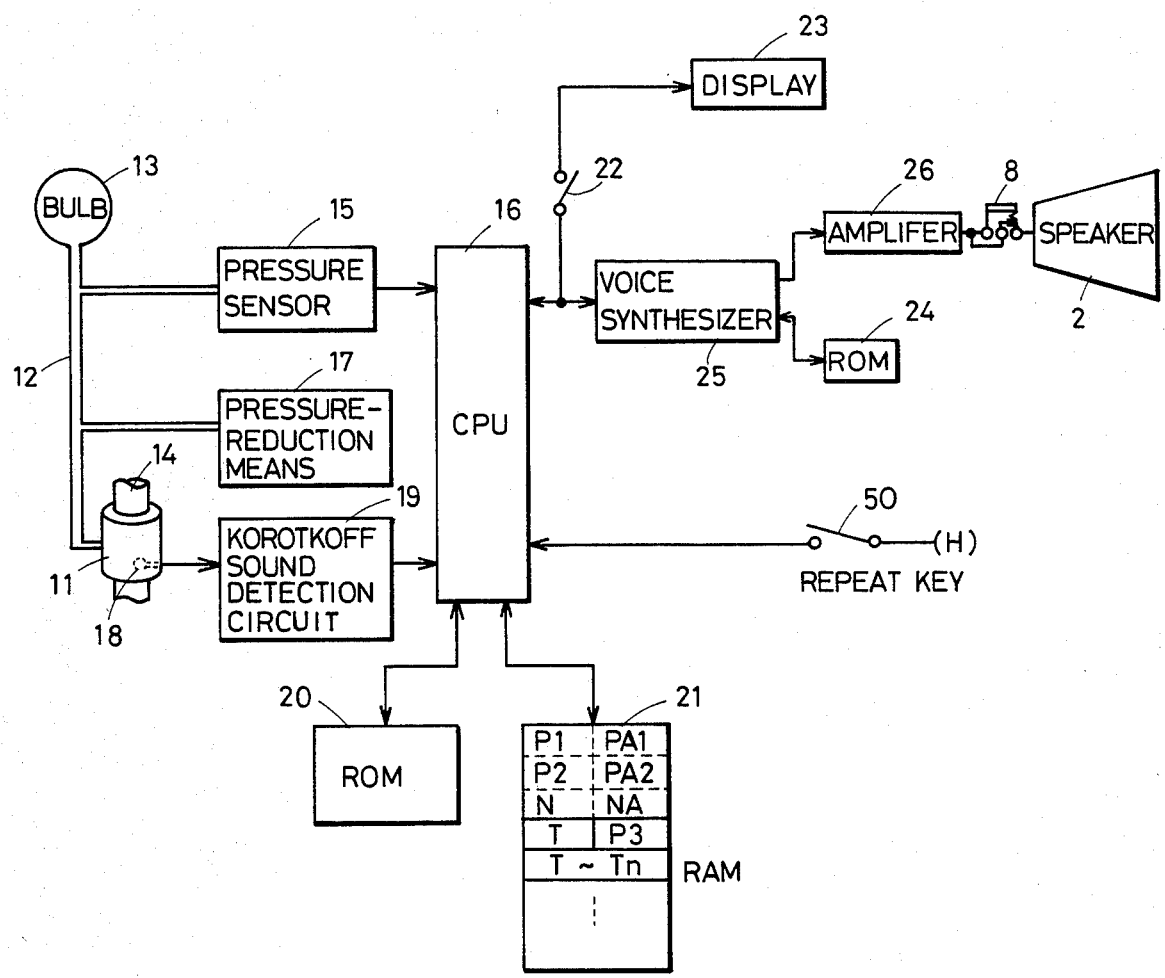
Figure 6:
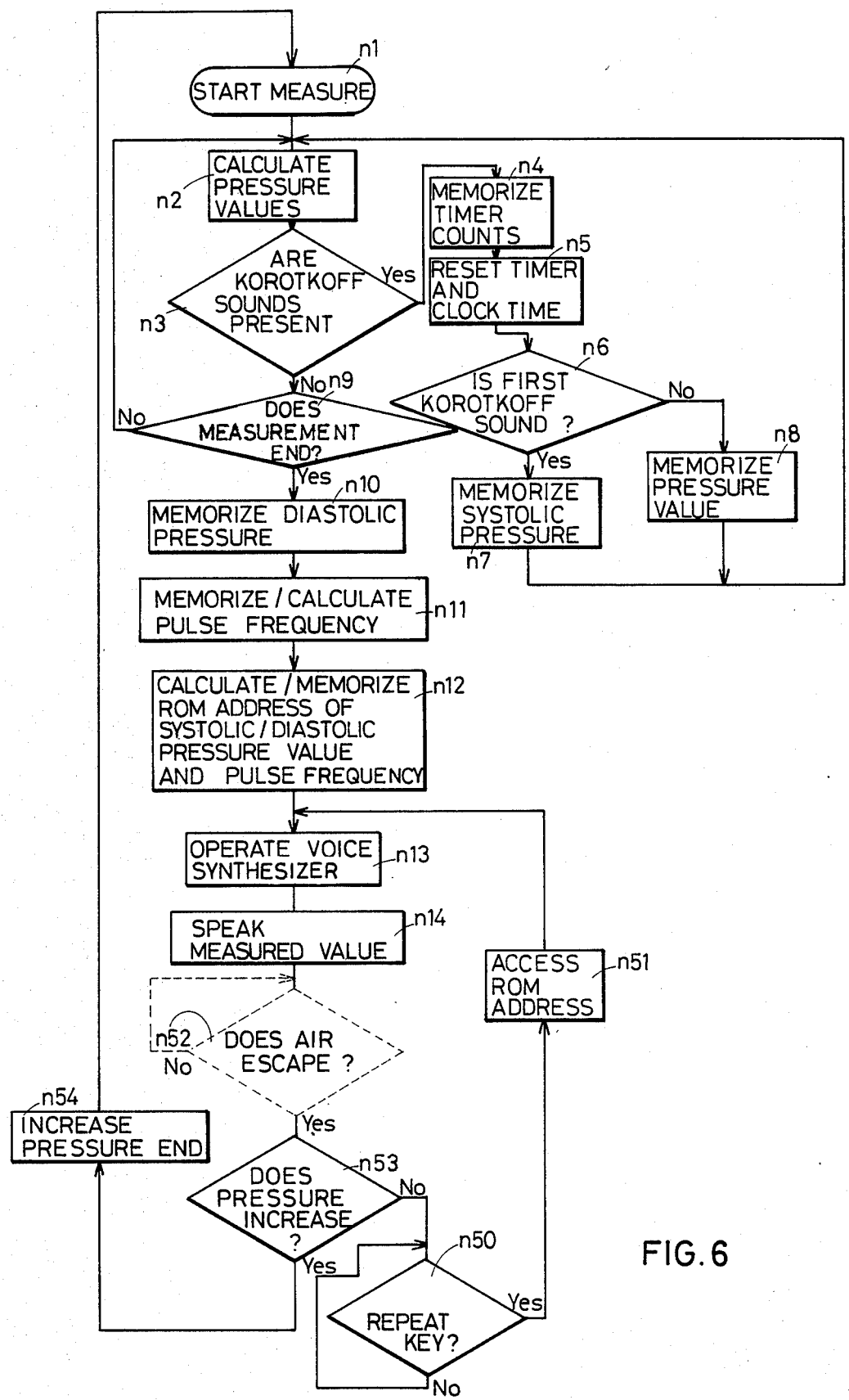
FIG. 6 shows an operational flow chart of the sphygmomanometer of another preferred embodiment of the present invention.

Next, another preferred embodiment of the present invention is described below. FIG. 5 shows a block diagram of a blood pressure measuring device as another preferred embodiment of the present invention. FIG. 6 shows the operational flow chart of a blood pressure measuring device as a still further embodiment of the present invention. Some of the components shown in FIGS. 5 and 6 are identical to FIGS. 2 and 3, which are represented by the identical symbols, while the description of these is deleted.

In another preferred embodiment of the present invention, repeat instruction keys 5, 6, and 7 shown in FIG. 2 are substituted by a single repeat key 50. In other words, the repeat instruction key 50 does not individually activate repeating the systolic and diastolic pressure values, but activates repeating these values sequentially. However, even if three of the repeat instruction keys are provided, as explained hereinbelow, these keys are inhibited from being activated while the blood pressure measuring operation is still underway. In another preferred embodiment, as shown in FIG. 6, operation signal activated by the repeat instruction key 50 can be accepted only during a period from the end of the blood pressure measuring operation until the start of the next measuring operation, i.e., between a period after the step n9 identifies the end of the measuring operation and then the measured value is informed by speech means, while said period ranges until the state of the next operation to pressurize the arm cuff 11 is identified by step n53, or the operation signal activated by the repeat instruction key 50 can be activated after the blood pressure measuring operation is completed, and also after the pneumatic pressure is discharged from the arm cuff 11 to a level below 20 mmHg. Operation signal of the repeat instruction key 50 can be accepted only during a period from a time when the stop n52 identifies that the measuring operation is ready, and up to a time when the step n53 identifies that the arm cuff 11 is pressurized. As a result, the operational state of the repeat instruction key 50 is detected by the CPU 16 during step n50. On receipt of a signal output from the repeat key 50, the CPU 16 reads the voice data address of ROM 24, which corresponds to the measured blood pressure values memorized in the memory areas P1, P2, and NA of RAM 21, then the CPU 16 feeds the address to the voice synthesizer 25 together with the control signal, and then the operation mode proceeds to step n13. During the step n13, being activated by the control signal fed from the CPU 16 and address data of ROM 24, the voice synthesizer 25 again reads the memory contents of ROM 24 and synthesizes a voice signal corresponding to the measured blood pressure value, and finally and sequentially repeats the measured values memorized in memory areas P1, P2, and N by speech using speaker 2 (step n14).

In such a manner as described above, during step n50, the CPU 16 detects that the repeat instruction key 50 is being pressed, and then the operation mode proceeds to step n51, n13, and n14, where the blood pressures are measured, and then the previously measured values are repeated by means of speech.

As a result, after the blood pressure measuring operation is completed and then the result is informed by speech, it becomes possible to repeat the measured value previously spoken by speech by operating the repeat instruction key 50 until the next measuring operation starts, or during a period from the end of the measuring operation up to the start of the next measuring operation after the pneumatic pressure is discharged from the arm cuff 11. As indicated by FIG. 6, ROM 20 is provided with operation programs, which inhibits accepting any operation of the repeat instruction key 50 during a period from the start of pressurizing the arm cuff 11 ("Being pressurized"—Yes, as identified through the step n53) until the blood pressure measuring operation ends (step n14), or until the pneumatic pressure is discharged ("Discharge completed"—Yes, as identified through the step n52). As a result, the speech repeat operation is inhibited during this period. Except this period, all the operations of the repeat instruction key 50 are watched by the step 50n, and so the result of the last blood pressure measuring operation can be repeated by operating the repeat instruction key 50 whenever necessary.

Figure 7:
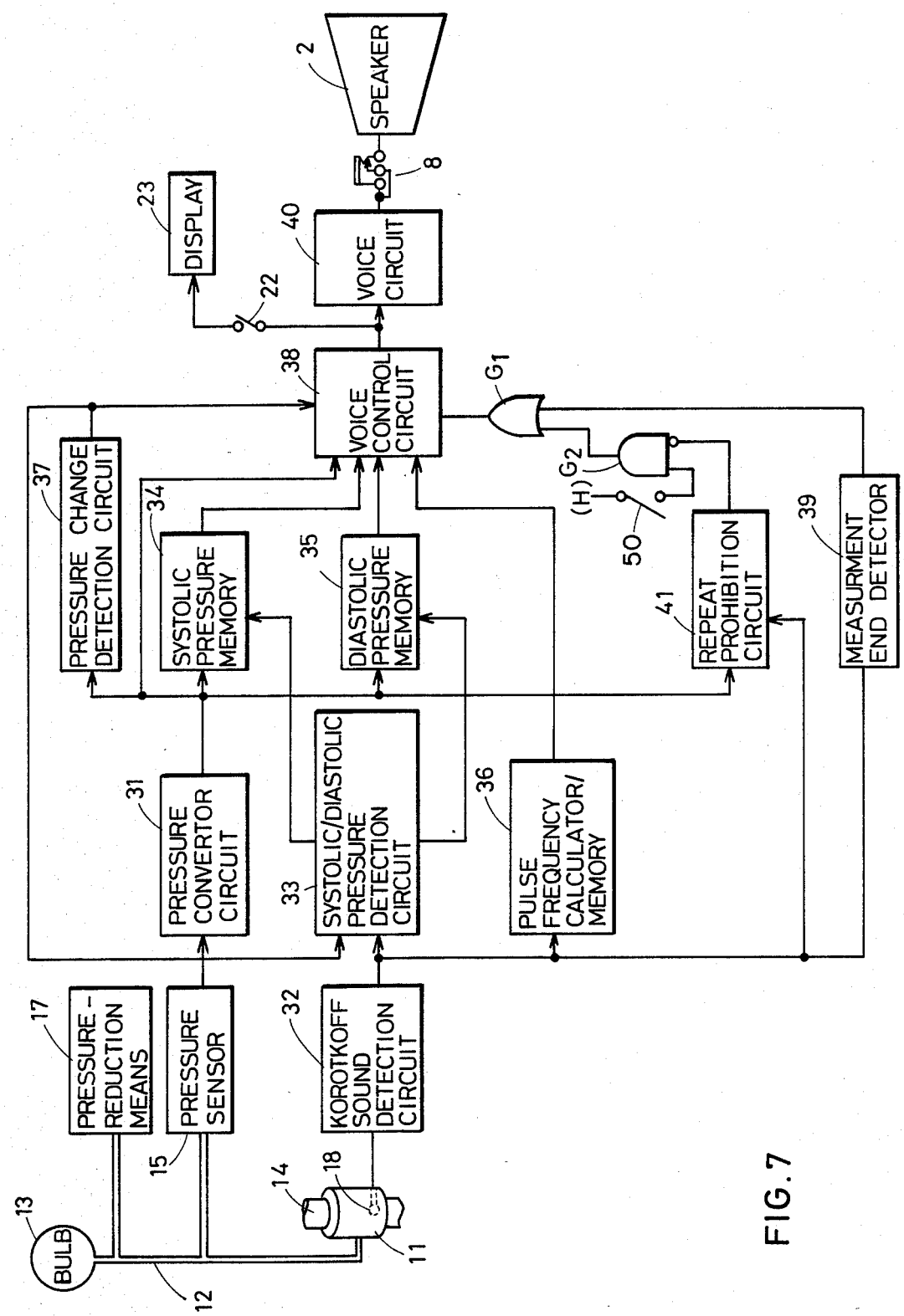
FIG. 7 shows a block diagram of the construction of the sphygmomanometer of a further embodiment of the present invention.

FIG. 7 shows a simplified block diagram of a sphygmomanometer of a still further embodiment of the present invention. In FIG. 7, those components identical to FIG. 4 are represented by the same symbols and description of these is deleted. Using the Korotkoff sound fed from the Korotkoff sound detection circuit 32, the blood pressure measurement end detection circuit 39 identifies a condition, for example, a state where the Korotkoff sound is not being fed for more than 5 seconds, then detects that the blood pressure measuring operation is completed, and finally feeds its output to the voice control circuit 38 through OR gate G1.

The repeat prohibition circuit 41 receives a blood pressure value output from the pressure converter circuit 31 and an output from the Korotkoff sound detection circuit 32, thus enabling said circuit 41 to gain access to the pressurized condition of the arm cuff 11 whether it is increased or decreased. Then, it detects the existing process from the beginning of the blood pressure measuring operation (where said circuit 41 detects that the pneumatic pressure is increasing in the arm cuff 11) until the end of the blood pressure measuring operation (where said circuit 41 detects the last Korotkoff sound), or the existing process from the beginning of the blood pressure measuring operation until the pneumatic pressure is discharged from the arm cuff 11 (where the pneumatic pressure drops, for example, below 20 mmHg), while this circuit 41 feeds an inhibition signal to inhibit the input of the AND gate G2 so that the output from the repeat instruction key 50 that enters the input of the AND gate G2 can not be fed to the voice control circuit through the AND gate G2 and OR gate G1. Said voice control circuit 38 is activated in responding to a signal representing the state of supplying pressure to the pressure change detection circuit 38, or in responding to a signal output from OR gate G1.

Except the operation described above, all the blood pressure measuring operations are executed as shown in FIG. 3, and the results are informed by speech. Method of repeating the measured blood pressure values is described below.

In responding to the end of either the blood pressure measuring operation or the end of the pneumatic pressure discharge from the arm cuff 11, an inhibition signal output from the repeat prohibition circuit 41 is freed, and so AND gate G2 is open. During this state, when the repeat instruction key 50 is activated, the operation signal is fed to the voice control circuit 38 through AND gate and OR gate G1, while in responding to this signal, the voice control circuit 38 then outputs a control signal that receives the measured value memorized by the memory circuits 34, 35, and 36, together with the ROM address signal. After receiving these signals, the voice circuit 40 synthesizes a voice signal that matches the measured value, which is then fed to speaker 2 which eventually repeats speaking of the measured blood pressure values.

The repeat prohibition circuit 41 detects that the pneumatic pressure has increased in the arm cuff 11 and outputs an inhibition signal so that AND gate G2 will be closed. As a result, the output from the repeat instruction key 50 is inhibited during a period from the beginning of pressurizing the arm cuff 11 until either the blood pressure measuring operation or pneumatic pressure discharge from the arm cuff 11 is terminated, and except such a period mention above, the output from the repeat instruction key 50 is effectively input to the voice control circuit 38 which eventually enables speaker 2 to repeat speaking of the measured blood pressure values.

In the above embodiment of the present invention, a repeat key commonly available for the respective measured values is used as the means for instructing to repeat speaking of such measured values. It should be understood, however, that the present invention is not limitative of the spirit and scope of the embodiment described above, for example, a variety of modifications and variations can be developed, wherein a plurality of the repeat instructing keys can be provided according to the number of the measured values, with which a plurality of the measured values can be individually repeated.

The preferred embodiments shown in FIGS. 2 and 5 have respectively made it possible to memorize the ROM 24 address calculated by the CPU 16 in the memory areas PA1, PA2, and NA. The present invention is not defined within these embodiments, for example, the ROM 24 address may be calculated whenever the repeat instruction is fed to the CPU 16.

The present invention being thus described, it will be obvious that the same may be varied in many ways. Such variations are not to be regarded as a departure from the spirit and scope of the present invention, and all such modifications are intended to be included within the scope of the following claims.

What is claimed is:
1. A sphygmomanometer comprising:
a pressure cuff;
pressure detection means for detecting the pressure in said cuff;
means associated with said cuff for detecting Korotkoff sounds;
means for determining systolic and diastolic pressure values in accordance with outputs from the pressure detection means and Korotkoff sound detection means;
memory means for storing data representing the systolic and diastolic pressure values determined by said determining means;
end detection means for detecting the end of a measuring operation;
output means for audibly outputting the data stored in said memory means representing said pressure values in response to output from the measuring operation end detection means; and
repeat signal input means for actuating said output means to audibly repeat output of the data stored in said memory means;
wherein said output means is responsive to said repeat signal input means for audibly repeating the data stored in said memory means.

2. The device of claim 1, comprising
means for also determining at least pulse frequency;
means for storing separately data representing each of said systolic and diastolic pressures and said pulse frequency;
said repeat signal input means comprising a plurality of individual actuators corresponding to at least said systolic and diastolic pressures and said pulse frequency, respectively;
wherein said output means is responsive to said individual actuators of said repeat signal input means for audibly and individually repeating one of said systolic pressure, diastolic pressure and pulse frequency.

3. The device of claim 1, further comprising initiation detection means for detecting initiation of a measuring operation by said device; and
inhibiting means responsive to said initiation detection means for inhibiting operation of said repeat signal input means during a measuring operation.

4. A sphygmomanometer according to claim 3 wherein said inhibiting means inhibits operation of said repeat signal input means during a period at least from the start of pressurizing of said cuff until a blood pressure measuring operation is completed.

* * * * *